United States Patent [19]

Malabarba et al.

[11] Patent Number: 4,882,419

[45] Date of Patent: Nov. 21, 1989

[54] PROCESS FOR PREPARING ANTIBIOTIC L 17392 (DEGLUCOTEICOPLANIN)

[75] Inventors: Adriano Malabarba, Milan; Paolo Strazzolini, Fiume Veneto; Bruno Cavalleri, Milan, all of Italy

[73] Assignee: Gruppo Lepetit S.p.A., Milan, Italy

[21] Appl. No.: 845,268

[22] PCT Filed: Jun. 4, 1985

[86] PCT No.: PCT/EP85/00267

§ 371 Date: Feb. 6, 1986

§ 102(e) Date: Feb. 6, 1986

[87] PCT Pub. No.: WO86/00076

PCT Pub. Date: Jan. 3, 1986

[30] Foreign Application Priority Data

Jun. 13, 1984 [GB] United Kingdom ............... 8415093

[51] Int. Cl.$^4$ ........................ C07K 7/50; C07K 1/00; C07K 1/14
[52] U.S. Cl. ................... 530/317; 530/333; 530/344; 530/335; 530/336
[58] Field of Search ............. 530/317, 333, 335, 336, 530/344

[56] References Cited

U.S. PATENT DOCUMENTS 3,960,828  6/1976  Meienhofer ..................... 530/328
4,293,490 10/1981  Abbott et al. ................... 530/317
4,322,343  3/1982  Debono .......................... 424/118
4,497,802  2/1985  Debono .......................... 424/118

FOREIGN PATENT DOCUMENTS 0090578 10/1983  European Pat. Off. .
0100605  2/1984  European Pat. Off. .
0132116  1/1985  European Pat. Off. .
2121401 12/1983  United Kingdom .
2148303  5/1985  United Kingdom .

OTHER PUBLICATIONS

Malabarba et al., Journal of Antibiotics, vol. XXXVII, No. 9, pp. 988–999, (911984).

Barna et al., Journal of Antibiotics, vol. XXXVII, No. 10, pp. 1204–1208, (10/1984).
Hunt et al., J. Am. Chem. Soc. vol. 106, No. 17, pp. 4891–4895, (8/22/84).
Barna et al., J. Am. Chem. Soc., vol. 106, No. 17, pp. 4895–4902, (8/22/84).
Cram et al., Organic Chemistry, Second Ed. McGraw-Hill Book Company, New York, P. 559 (1964).

Primary Examiner—Margaret Moskowitz
Assistant Examiner—Christina Chan
Attorney, Agent, or Firm—Stephen L. Nesbitt

[57] ABSTRACT

Process for preparing antibiotic L, 17392 by catalytically hydrogenating a deglucoteicoplanin ester of formula

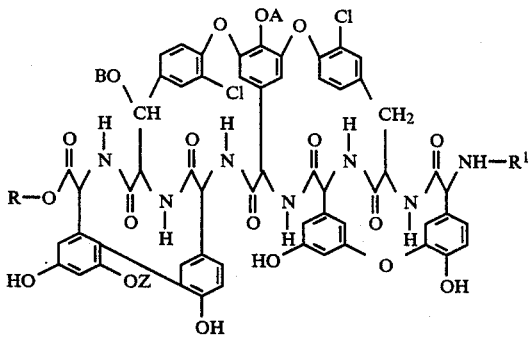

Formula II wherein A, B and Z represent hydrogen atoms, R represents benzyl or substituted benzyl, wherein the phenyl group is substituted with at least a substituent selected from chloro, bromo, fluoro, nitro, $(C_1-C_3)$alkyl, $(C_1-C_3)$alkoxy and the like, with the exclusion of the tri-nitro phenyl group, or acid addition salts thereof, to catalytic hydrogenolysis in the presence of a poisoned hydrogenation catalyst at a temperature from 10° C. to 40° C. and a pressure between ambient pressure and 5 atm, in an inert organic solvent preferably in the presence of a mineral acid.

11 Claims, No Drawings

PROCESS FOR PREPARING ANTIBIOTIC L 17392 (DEGLUCOTEICOPLANIN)

Antibiotic L 17392 is an antibiotic substance which is obtained by removing all the sugar moieties from the glycopeptidic antibiotic teicoplanin. Teicoplanin is the international non-proprietary name (INN) of the antibiotic substance formerly named teichomycin which is obtained by cultivating the strain *Actinoplanes teichomyceticus* nov. sp. ATCC 31121 in a culture medium containing assimilable sources of carbon, nitrogen and inorganic salts (see U.S. Pat. No. 4,239,751). According to the procedure described in the above cited patent an antibiotic complex containing teichomycin $A_1$, $A_2$ and $A_3$ is recovered from the separated fermentation broth by extraction with a suitable water insoluble organic solvent and precipitation from the extracting solvent according to common procedures. Teichomycin $A_2$, which is the major factor of the isolated antibiotic complex, is then separated from the obtained antibiotic mixture by means of column chromatography on Sephadex ®.

PHYSICO-CHEMICAL CHARACTERISTICS OF CRYSTALLINE PURE ANTIBIOTIC L 17392

(a) it is soluble in water at a pH higher than 9 and aqueous methanol, ethanol and acetone; slightly soluble in ethyl alcohol and dimethylformamide (b) an ultraviolet absorption spectrum which shows the following absorption maxima:
in 0.1N hydrochloric acid: $\lambda_{max}$ 279 nm ($E_1\, cm^{1\%} = 87.1$)
in 0.1N sodium hydroxide: $\lambda_{max}$ 297 nm ($E_1\, cm^{1\%} = 165.3$)

(c) an infrared absorption spectrum in nujol with the following mainly significant absorption maxima ($cm^{-1}$):
3250 ($\nu$NH; and phenolic $\nu$OH)
1645 (Amide I)
1610 ($\nu$COO$^-$)
1595 ($\delta$NH$_3^+$)
1520 (Amide II)

(d) Some of the $^1$H NMR data obtained after $D_2O$ exchange and selective decoupling experiments of the $^1$H NMR spectrum registered at 270 MHz with a Bruker WH-270 Spectrometer, in DMSO-$d_6$ at 50° C. (internal standard TMS, $\delta = 0.00$ ppm) are as follows: ($\delta$, multiplicity):
2.85–3.30, 2 dd; 4.12, dd; 4.37, d; 4.45, d; 4.50, s; 5.00, ddd; 5.11, d; 5.14, d; 5.35, d; 5.56, d; 5.60, d; 6.3–7.9, m; 6.55, d; 7.37, d; 7.50, d; 7.61, d; 8.26, d; 8.28, d; 8.5–10.2, br;
d = doublet
dd = doublets of doublets
ddd = doublet of doublets of doublets
s = singlet
m = multiplet
br = broad (e) an elemental analysis which indicates the following approximate percentage composition (average): carbon 58.05%; hydrogen 3.58%; nitrogen 8.23%; chlorine 5.85%; (after correction for a weight loss of 11%, measured by thermal gravimetric analysis)

(f) a molecular weight of 1199, confirmed also by FAB-MS analysis (g) the following formula [calculated on the basis of the available data]:

$C_{58}H_{45}Cl_2N_7O_{18}$ (h) a retention time ($t_R$) of 12.2 min when analyzed by HPLC using a pre-column (5 cm) packed with Perisorb RP-8 (30 μm; Merck) followed by a column Hibar RT 250-4 (Merck) prepacked with LiChrosorb RP-8 (10 μm) and eluting with a liner step-gradient ranging from 10% to 30% acetonitrile in 0.2% aqueous ammonium formate; flow rate: 2 ml/min. (internal standard: Teicoplanin $A_2$ component 2 of U.K. Patent Application Publication 2121401, $t_R = 22.4$ min)

(i) an acidic function capable of forming salts (l) a basic function capable of forming salts (m) no sugar residue On the basis of the chemico-physical data the following formula may be attributed to antibiotic L 17392:

(formula I)

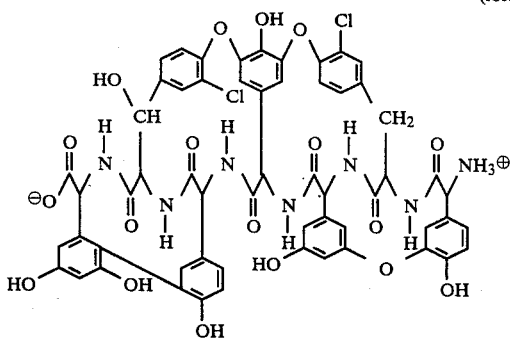

A substance having the same structural formula is disclosed in European Patent Application No. 0098578 and is named antibiotic A 41030 factor B. This substance is obtained by mans of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030 factor B, included.

Antibiotic L 17392 possesses acid and basic functions capable of forming salts with bases and acids, respectively. The acid and/or basic salts of antibiotic L 17392 can be in general prepared according to known per se procedures.

These procedures includes reacting antibiotic L 17392 with at least a molar equivalent of the selected acid or base.

A preferred procedure for preparing a salt of antibiotic L 17392 with a base includes reacting antibiotic L 17392 and the base in about equimolecular amount in water, conveniently at room temperature, and lyophilizing the solution obtained at the end of the salification reaction.

A preferred procedure for preparing a salt of antibiotic L 17392 with an acid includes reacting antibiotic L 17392 with the selected acid in an aqueous lower alkanol, conveniently at room temperature. Then, the water is eliminated and the desired salt of antibiotic L 17392 is precipitated by adding a non-solvent, such as ethyl ether, to the organic phase. A preferred example of aqueous lower alkanol is a mixture of water and butanol. The preferred ratio water/butanol is about 30:70.

Representative examples of salts of antibiotic L 17392 with bases are the alkali metal, such as sodium or potassium, the ammonium and alkylammonium salts. These salts with bases encompass also the salts with basic amino acids such as lysine and arginine.

Representative examples of salts of antibiotic L 17392 with acids are the hydrochloric, hydrobromic, sulfuric, phosphoric, glycolic, lactic, pyruvic, malonic, succinic, fumaric, malic, tartaric, citric, ascorbic, maleic, hydroxymaleic, benzoic, hydroxybenzoic, phenylacetic, cinnamic, 2-phenoxybenzoic, methanesulfonic and 2-hydroxyethanesulfonic acid additions salts.

The in vitro antibacterial activity of L 17392 was determined using the two-fold dilution method in microtiter system. Todd-Hewitt broth (Difco) was used for streptococci and Isosensitest broth (Oxoid) for staphylococci and gram-negative bacteria. Overnight broth cultures were diluted so that the final inoculum was about $10^4$ colony-forming units per ml (cfu/ml). Minimal inhibitory concentration (MIC) was read as the lowest concentration which showed no visible growth after 18-24 h incubation at 37° C. The obtained results are reported in Table I below:

TABLE I

| In vitro antibacterial activity of L 17392 | |
|---|---|
| Organism | MIC (μg/ml) antibiotic L 17392 |
| Staphylococcus aureus ATCC 6538 | 0.025 |
| Staplylococcus aureus Tour | 0.05 |
| Staphylococcus aureus Tour[a] | 0.2 |
| Staphylococcus aureus Tour[b] | 0.2 |
| Staphylococcus epieermidis ATCC 12228 | 0.0125 |
| Streptococcus pyogenes C 203 | 0.05 |
| Streptococcus pneumoniae UC 41 | 0.05 |
| Streptococcus faecalis ATCC 7080 | 0.1 |
| Escherichia coli SKF 12140 | 25 |
| Proteus vulgaris × 19 H ATCC 881 | 50 |
| Pseudomonas aeruginosa ATCC 10145 | >100 |

[a]Inoculum: $10^6$ cfu/ml
[b]Determined in the presence of 30% bovine serum

Antibiotic L 17392 was found to be very active against staphylocci (*S. aureus, S. epidermidis*). In particular, it was very effective against various clinical isolate methicillin-resistant staphylococci (*S. aureus, S. epidermidis*). Some experimental results are reported in Table II:

TABLE II

| Organism | MIC (μg/ml) |
|---|---|
| S. aureus L 1096 | 0.05 |
| S. aureus L 1097 | 0.05 |
| S. aureus L 1524 | 0.1 |
| S. aureus L 1526 | 0.05 |
| S. epidermidis L 785 | 0.05 |
| S. epidermidis L 835 | 0.05 |
| S. epidermidis L 1142 | 0.05 |
| S. epidermidis L 1372 | 0.2 |
| S. epidermidis L 1378 | 0.05 |

It is known that the removal of all sugars moieties from a complicated molecule such as a glycopeptidic antibiotic substance always has many difficulties. In fact, mild acid conditions usually produce only a partial removal of the sugar moieties while stronger acid hydrolysis conditions may promote partial degradation of the substrate and/or changes in the stereochemical configuration of the chiral centers. For instance, the true aglicone of the glycopeptide antibiotic named avoparcin has never been isolated, since for this substance, as with similar substances, it has not yet been possible to devise selective hydrolysis conditions capable of removing all the sugar moieties without altering the "core peptide" structure. The following scientific literature supports the above considerations: G. A. Ellestad et al., J. Antibiotics, 36, 1683 (1983); C. M. Harris et al., J. Am. Chem. Soc., 105, 6915 (1983); W. J. McGahren et al., J. Antibiotics, 36, 1671 (1983).

There is no indication whatsoever in the above cited literature which suggests using any specific hydrolysis condition to transform a teicoplanin compound or teicoplanin-like compound into the corresponding teicoplanin aglycone (antibiotic L 17392 or deglucoteicoplanin). Moreover, the removal of all the sugar moieties from a teicoplanin-like compound (as herein below defined) to give antibiotic L 17392 must take place without simultaneously provoking any modification or alteration of the chemical structure or chiral centers of the substrate, since these modifications affect the biological activity of the resulting substance unfavorably.

The process of the present invention is directed to the production of antibiotic L 17392 by submitting a suitable deglucoteicoplanin ester to catalytic hydrogenolysis.

This deglucoteicoplanin ester may be one of the ester derivatives at the carboxy function of the aglycone moiety of teicoplanin characterized by having the ester bond which is cleavable by means of catalytic hydrogenation.

Representative examples of deglucoteicoplanin esters which are suitable starting materials in the process of the invention are: benzyl, substituted benzyl, benzhydryl, 4-picolyl esters and the like.

The term "substituted benzyl" indicates a phenylmethyl group which is substituted at the phenyl ring with at least one substituent, and preferably from 1 to 3 substituents, selected from chloro, bromo, fluoro, nitro, ($C_1$-$C_3$)alkyl, ($C_1$-$C_3$)alkoxy and the like, with the exclusion of the tri-nitro phenyl group. Example of said substituted benzyl groups are: 3-chlorobenzyl, 4-chlorobenzyl, 2,3-dichlorobenzyl, 2,4-dichlorobenzyl, 2,4,6-trichlorobenzyl, 3-fluorobenzyl, 4-fluorobenzyl, 3-methylbenzyl, 3-methoxybenzyl, 2-ethoxybenzyl, and the like.

The catalyst employed in the hydrogenolysis of the invention may be one of a number of known catalysts, such as Palladium, nickel, Copper, Cobalt either at the zero-valent state and/or with positive oxidation numbers on suitable supports as known in the art, provided that they are used as "poisoned" catalysts.

A preferred metal catalysts is Palladium on a support selected from carbon, barium carbonate, barium sulfate, and calcium sulfate. Good results in the process of the invention are obtained by using 5-10% Palladium on barium sulfate. This catalyst is the most preferred one. The reaction is generally conducted in an inert organic solvent, i.e. an organic solvent which does not unfavorably interfere with the reaction course.

Representative examples of suitable inert organic solvents are lower alkanols which are liquid at the reaction temperature and preferably those which are liquid at room temperature such as methanol and ethanol, dioxane, glycols and glycol monoalkyl ethers, such as ethylene glycol and ethylene glycol monomethyl ether.

Generally, the reaction is conducted in an acidic medium.

Preferred acids to be added to the eaction mixture are rather strong mineral acids, such as hydrohalidic acid, e.g. hydrochloric acid.

The pressure of the reaction medium is, in general, a critical parameter and depends mainly on the type of catalyst used. Generally, it may be between ambient pressure and about 5 atm.

The reaction temperature depends on the selected catalyst and pressure. The preferred temperature is room temperature, however, a temperature from 10° C. to 40° C. can be employed, if necessary.

When the catalyst is 5-10% Palladium on barium sulfate in the presence of mineral acid, the process of the invention is advantageously carried out at room temperature and pressure. In this case, in fact, it is not necessary either to increase the temperature or the pressure since the reaction is completed in a reasonable period of time (0.5-3 h) and with very high yields (80-90%).

When the process of the invention is conducted on an essentially pure deglucoteicoplanin ester or acid-addition salt thereof essentially pure antibiotic L 17392 is obtained.

The reaction course can be easily monitored as known in the art by means of TLC or HPLC procedures using for instance UV or autobiographic detection. UV detection is made at about 254 nm, while authobiographic detection is made using microorganisms which are susceptible to the teicoplanin antibiotics.

The theoretical amount of hydrogen used in the process of the invention is about 1 mole per mole of ester substrate. Generally, as known in the art, a slight excess of hydrogen is necessary to complete the reaction.

The reaction product is then recovered and purified by means of known per se techniques such as precipitation by non-solvents, extraction with solvents, crystallization from solvents and chromatographic procedures, such as column chromatography and reverse-phase column chromatography.

As already said, when a rather purified starting material is used, the resulting antibiotic L 17392 has an acceptable purity. If a further purification of antibiotic L 17392 is necessary or desired, it can be obtained according to usual purification techniques and, in particular, by chromatography, such as "reverse-phase" high performance liquid chromatography (HPLC) and column chromatography.

A preferred purification procedure involves the use of a reverse phase column chromatography. The preferred adsorbent in this case is a silanized silica gel having a distribution particle range from 0.06 to 0.2 mm. The eluent can be one of the hydrophilic mixtures that are used in this purification technique. Representative examples of these hydrophilic eluents are the mixtures of diluted aqueous solution of ammonium salts of organic acids, acetonitrile or water soluble lower alkanols. Representative examples of diluted aqueous solutions of ammonium salts of organic acids are a 0.1-6% ammonium formate aqueous solutions, while examples of suitable alkanols are methanol, ethanol, propanol and the like. Preferred eluents are mixtures of aqueous ammonium formate and acetonitrile at a pH between 6 and 8 or a mixtures of aqueous ammonium formate and methanol. A preferred procedure includes a first reverse phase chromatography on silanized silica gel (0.06-0.2 mm) developing with a linear step gradient of 5 to 21% acetonitrile in 0.2% aqueous ammonium formate and a second column chromatography which uses a mixture of acetonitrile/water 1:1 as the eluent.

Another preferred procedure includes:

(a) mixing a solution of the crude antibiotic in 0.2% aqueous ammonium formate/methanol/n-butanol, 1:2:3, with silanized silica gel and stripping off the solvents, (b) applying the residue at the top of a silanized silica gel (0.06-0.2 mm) column, developing with 0.6% aqueous ammonium formate and acetonitrile, 9:1, discarding the eluate and continuing the elution with a linear gradient of acetonitrile in water from 1:9 to 4:6.

An example of the way in which the course of the reaction process of the invention may be monitored or the reaction product titrated by HPLC is as follows: samples are drawn from the reaction mixture at predetermined times, diluted to a final concentration of about 2 mg/ml in a mixture 0.2% ammonium formate/acetonitrile, 50:50 (v/v) and injected (20 μl) into the HPLC system. The HPLC system is a chromatograph Varian 5000 equipped with 20 μl loop injector Rheodyne 7125; a UV detector at 254 nm and a pre-column packed with Perisorb RP-8 Merck (30-40 μm) followed by a Hibar Merck column (25 cm) pre-packed with LiChrosorb RP-8 (10 μm) Eluent: a linear gradient from 5% B in A to 60% B in A in 30 min, at a flow rate of about 3 ml/min; solution A: 0.2% aqueous ammonium formate; solution B: acetonitrile.

The product obtained according to the above procedure is essentially pure antibiotic L 17392 which possess satisfactory physico-chemical and biological characteristics for the use according to the present description. Antibiotic L 17392 can also be obtained as a crystalline pure substance either directly from a crude reaction product or by treatment of substantially pure antibiotic L 17392.

Crystalline pure antibiotic L 17392 is in fact obtainable by suspending the substantially pure amorphous antibiotic in a mixture of water and acetonitrile, 9:1 at a pH of about 1.7. The pH is conveniently adjusted by adding 1N hydrochloric acid. The resulting solution is purified by column chromatography and then the pooled antibiotic L 17392 containging-fractions are left aside about 24 h to permit the precipitation of the crystalline antibiotic L 17392.

A preferred column chromatography procedure in this case comprises applying the acidic solution to a silanized silica gel column equilibrated with diluted aqueous ammonium formate, washing with water and developing with a linear gradient of acetonitrile in water from 10% to 40%; flow rate 70 ml/h, for 30 h.

This procedure can also be applied directly to crude antibiotic L 17392 or to a solution of crude antibiotic L 17392 as obtained after remotion of the catalyst at the end of the hydrogenolysis process herein described. Antibiotic L 17392 crystals are colorless needles.

The term "essentially pure" as referred to an antibiotic substance of the present disclosure refers to substances having an HPLC titer greater than 95% (percent of the areas of the peaks, at the pre-determined UV wavelength, generally 254 nm), a water and solvents content from 10 to 15% (by weight) and an inorganic residue lower than 0.5% (by weight). The deglucoteicoplanin ester derivatives which are the starting materials of the process of the invention are represented by the following formula II

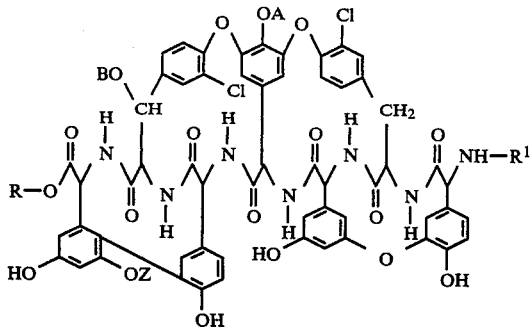

wherein R is the alkyl residue of an alcohol which forms an ester bond with the adjacent carboxy group which is cleavable by means of catalytic hydrogenolysis, as above defined, and A, B and Z represent hydrogen atoms. These deglucoteicoplanin esters are prepared by submitting a suitable teicoplanin-like substance to an esterification process under controlled conditions. For convenience herein, the term "teicoplanin-like" substance or substrate represents a compound selected from teicoplanin, a teicoplanin factor, antibiotic L 17054, antibiotic L 17046, and mixtures thereof in any proportion.

Some of these teicoplanin-like substances are represented by the above formula II wherein R and $R^1$ represent hydrogen, A is hydrogen or N-[($C_{10}$–$C_{11}$)aliphatic acyl]-β-D-glucosamine, B is hydrogen, or a N-acetyl-β-D-glucosamine, and Z is hydrogen or α-D-mannose. As already said, teicoplanin is an antibiotic substance obtained by *Actinoplanes teichomyceticus* ATCC 31121 and is disclosed in U.S. Pat. No. 4,239,751.

British Patent Application Publication No. 2121401 discloses that antibiotic teicoplanin (formerly teichomycin) factor $A_2$ is a mixture of five closely related co-produced components. According to recent structural studies it is possible to represent teicoplanin $A_2$ components 1, 2, 3, 4 and 5 by the above formula I wherein R and $R^1$ are both hydrogen, A is N-[($C_{10}$–$C_{11}$)aliphatic acyl]-β-D-glucosamine group, B is a N-acetyl-β-D-glucosamine group and Z is a α-D-mannose group.

All these sugar moieties, when present, are linked to the teicoplanin nucleus through O-glycosidic bonds. Representative and preferred examples of ($C_{10}$–$C_{11}$)aliphatic acyl groups are n-decanoyl, 8-methylnonanoyl, Z-4-decenoyl, 8-methyldecanoyl, and 9-methyldecanoyl.

Antibiotic L 17054 and antibiotic L 17046 are teicoplanin hydrolysis products. They are described in European Patent Application Nos. 84102666.9 and 84102665.1, respectively. They are obtained by submitting teicoplanin, a pure factor thereof or a mixture of any of said factors in any proportion, to selective hydrolysis which results in removing one or two sugar moieties of the starting material.

More particularly, the selective removal of N-[($C_{10}$–$C_{11}$)aliphatic acyl]-β-D-glycosamine gives antibiotic L 17054, while the selective removal of N-[($C_{10}$–$C_{11}$)aliphatic acyl]-β-D-glucosamine and α-D-mannose groups gives antibiotic L 17046.

Preferred hydrolysis conditions for the production of antibiotic L 17054 are: about 0.5N hydrochloric acid at a temperature between 70° and 90° C. and for a time which is generally between 15 and 90 min.

Antibiotic L 17054 is represented by the above formula II wherein R and $R^1$ are hydrogen atoms, A is hydroxy, B is N-acetyl-β-D-glycosamine and Z is α-D-mannose.

Preferred hydrolysis conditions for the preparation of antibiotic L 17046 are: about 1–3N hydrochloric acid, at a temperature between 50° and 90° C. and for a time which is generally between 30 and 60 min.

Antibiotic L 17046 is represented by the above formula II wherein R and $R^1$ are hydrogen atoms, A and Z are hydroxy groups and B is N-acetyl-β-D-glucosamine.

As already said, the deglucoteicoplanin esters of formula II are prepared by submitting a suitable teicoplanin-like substance to esterification under controlled conditions.

The reaction conditions of the esterification procedure are such that the "teicoplanin nucleus" is not modified and that all the sugar moieties of the starting material are hydrolyzed before the esterification is completed. A convenient procedure for preparing the deglucoteicoplanin ester intermediates of the invention includes reacting a teicoplanin-like compound with an excess of the suitable alcohol of formula ROH, wherein R is as above, in the presence of an acid catalyst such as 37% hydrochloric acid. Preferably, the alcohol of formula ROH is a liquid at the reaction temperature, so that it may act also as the reaction medium, without the need of adding another suitable solvent. The reaction is preferably conducted under reduced pressure. The reaction temperature is generally between 50° and 80° C., when the reaction pressure is about 20 mmHg. When necessary, portions of a mixture of the 37% hydrochloric acid with the suitable alcohol are added from time to time to reintegrate the portions of reaction medium which evaporates.

Portions of a suitable inert solvent capable of forming minimum azeotropic mixtures with water are also added and then the azeotrope which forms is distilled off under vacuum. Representative examples of solvents capable of forming minimum azeotropic mixtures with water are: benzene, toluene, butyl, ether, carbon tetrachloride, chloroform, cyclohexane, 2,5-dimethylfurane, hexane, nonane, m-xilene and the like.

These alternated operations of adding alcoholic hydrochloric acid followed by the minimum azeotrope-forming solvent and distilling the aqueous azeotrope which forms are repeated several times until the reaction is completed (i.e. the desired ester derivative is produced in acceptable or optimal yields).

PHYSICO-CHEMICAL CHARACTERISTICS OF DEGLUCOTEICOPLANIN BENZYL ESTER, HYDROCHLORIDE (a) IR registered in a nujol mull with a Perkin-Elmer 850 instrument: $\nu$ CO ester = 1730 $cm^{-1}$;
(b) a relative retention time

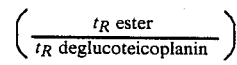

in the HPLC system reported above which is 1.69 ($t_R$ deglucoteicoplanin 11.4 min.).

(c) a pKa value of a sample dissolved in methylcellosolve®/water 4:1 which is 6.67
(d) UV absorption maxima (nm): 280 (in methanol); 279 (in 0.1N hydrochloric acid); 279 (in phosphate buffer pH 7.4); 298 (in 0.1N sodium hydroxide);
(e) elemental analysis (determined on samples previously dried at 140° C. under nitrogen atmosphere):
Found: C% 58.57; H% 4.14; N% 7.28; Cl% (total)[b] 7.90; Cl% (ionic)[b] 2.66; inorganic residue %[c] 0.2; weight loss %[d] 10.1.
Calculated for $C_{65}H_{51}Cl_2N_7O_{18}$: C% 58.90; H% 3.95; N% 7.40; Cl% (total)[b] 8.02; Cl% (ionic)[b] 2.67.

[b] Corrected for weight loss and inorganic residue
[c] Determined after heating the samples at 900° C. in oxygen atmosphere
[d] Determined by thermogravimetric analysis at 140° C.

PHYSICO-CHEMICAL CHARACTERISTICS OF ANTIBIOTIC L 17046

Antibiotic L 17046 has the following characteristics:
(a) the specific rotation $[\alpha]_D^{20}$ is $-44°$ (c=1%, DMF)
(b) it is freely soluble in water at pH>8.0, in dimethylformamide, dimethylsulfoxide, propyleneglycol and methylcellosolve; slightly soluble in methanol; almost insoluble in n-hexane, ethyl ether and acetone.
(c) it has an ultraviolet absorption spectrum that exhibits the following absorption maxima:
in 0.1N hydrochloric acid: $\lambda_{max}$ 278 nm ($E_{1\,cm}^{1\%}$=67.1)
in 0.1N sodium hydroxide: $\lambda_{max}$ 297 nm ($E_{1\,cm}^{1\%}$=124.1)
in phosphate buffer pH 7.4: $\lambda_{max}$ 277 nm ($E_{1\,cm}^{1\%}$=75.0)
(d) an infrared absorption spectrum in nujol with the following observable absorption maxima (cm$^{-1}$): 3700–2000, 2970–2850 (nujol), 1655, 1610, 1595, 1515, 1490, 1460 (nujol), 1375 (nujol), 1300, 1230, 1145, 1060, 1010, 890, 850, 820, 720 (nujol)
(e) an elemental analysis, after the sample has been previously dried at about 140° C. under inert atmosphere (weight loss=8.4%), which indicates the following approximate percentage composition (average): carbon 56.74%; hydrogen, 4.27%; nitrogen, 7.99%; chlorine, 5.11%; ashes, 0.6%.
(f) the following $R_f$ values in the TLC systems indicated below:

| Elution system (v/v) | $R_f$ value |
| --- | --- |
| (I) Acetonitrile/water 75:25 (silica gel Merck 60 F$_{254}$) | 0.53 |
| (II) Acetonitrile/5% aqueous sodium sulfate 30:70 (silica gel Merck silanized 60 F$_{254}$) | 0.54 |
| Visualization: UV-light at 254 nm; 3% ethanolic ninhydrine; 1% methanolic fluorescamine; | |

(g) a retention time ($t_R$) of 10.8 minutes when analyzed by reversed phase HPLC using a 150×4.0 mm Zorbax®ODS (5–6 µm) column (Zorbax is a trademark of the Dupont Co. for a octadecylsilane silica matrix), and eluting with a linear gradient from 0% to 50% solution B in solution A in 40 minutes
solution A: 25 mM NaH$_2$PO$_4$/acetonitrile (9:1) buffered at pH 6.0 with 0.1N NaOH
solution B: 25 mM NaH$_2$PO$_4$/acetonitrile (3:7) buffered at pH 6.0 with 0.1N NaOH), with a flow rate of 2 ml/min.; (internal standard: 3,5-dihydroxytoluene $t_R$ 5.60 minutes)
(h) Some of the $^1$H NMR data obtained after D$_2$O exchange and selective decoupling experiments are as follows (the $^1$H NMR spectrum is registered at 270 MHz in DMSO-d$_6$ at 60° C. and with a sample concentration of 20 mg/ml; internal standard, TMS δ=0.00 ppm): (δ ppm, multiplicity): 1.86, s; 2.81, d; 3.5, dd; ~3–4; 4.12, d; 4.32, d; 4.37, d; 4.56, s; 4.95, ddd; 5.07, s; 5.31, d; 5.39, s; 5.51, s; 5.66, d; 6.12, d; 6.29, s; 6.32, s; 6.37, d; 6.42, s; 6.60, d; 6.62, s; 6.64, d; 6.92, d; 7.90, s; 7.12, d; 7.21, d; 7.25, d; 7.43, d; 7.64, d; 7.66, d; 7.70, d; 7.85, s; 8.12, d; 8.46, d; ~9.5, s.
(i) a potentiometric titration profile which shows three titration slopes with pH$\frac{1}{2}$ values equal to 5.0 (one equivalent), 7.0 (one equivalent), and 11 (five equivalents) in methylcellosolve:water 4:1 upon titration with 0.01N NaOH of the solution of the test compound containing an excess of 0.01N in the same solvent mixture
(l) an acidic function capable of forming salts
(m) a basic function capable of forming salt
(n) a sugar residue which is N-acetyl-β-D-glucosamine.

PHYSICO-CHEMICAL CHARACTERISTICS OF ANTIBIOTIC L 17054

Antibiotic L 17054 has the following characteristics:
(a) the specific rotation $[\alpha]_D^{20}$ is $-34°$ (c=1%, DMF)
(b) it is freely soluble in water at pH>8.0, in dimethylformamide, dimethylsulfoxide, propylene glycol and methylcellosolve; slightly soluble in methanol; almost insoluble in ethyl ether and acetone.
(c) an ultraviolet absorption spectrum which has the following absorption maxima:
in 0.1N hydrochloric acid: $\lambda_{max}$ 278 nm ($E_{1\,cm}^{1\%}$=60.6)
in 0.1N sodium hydroxide: $\lambda_{max}$ 297 nm ($E_{1\,cm}^{1\%}$=118.8)
in phosphate buffer pH 7.4: $\lambda_{max}$ 277 nm ($E_{1\,cm}^{1\%}$=70.3)
(d) an infrared absorption spectrum in nujol with the following description maxima (cm$^{-1}$): 3700–2000, 2970–2850 (nujol), 1655, 1610, 1995, 1515, 1490, 1460 (nujol), 1375 (nujol), 1300, 1230, 1145, 1060, 1020, 970, 890, 850, 820, 720 (nujol)
(e) an elemental analysis, after the sample has been previously dried at about 140° C. under inert atmosphere (weight loss=7.8%), which indicated the following approximate percentage composition (average): carbon 55.46%; hydrogen, 4.50%; nitrogen 7.20%; chlorine 4.67%; ashes 0.2%.
(f) it has the following $R_f$ values in the TLC systems indicated below:

| Elution system (v/v) | $R_f$ value |
| --- | --- |
| (I) Acetonitrile/water 75:25 (silica gel Merck 60 F$_{254}$) | 0.32 |
| (II) Acetonitrile/5% aqueous sodium sulfate 30:70 (silica gel Merck silanized 60 F$_{254}$) | 0.61 |
| Visualization: UV-light at 254 nm; 3% ethanolic ninhydrine; 1% methanolic fluorescamine; | |

(g) a retention time ($t_R$) of 8.3 minutes when analyzed by HPLC using a 150×4.0 mm Zorbax® ODS (5–6 µm) column (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$/acetonitrile (9:1) buffered at pH 6.0 with 0.1 N NaOH; solution B: 25 mM NaH$_2$PO$_4$/acetonitrile (3:7) buffered at pH 6.0 with 0.1N NaOH), with a flow rate of 2 ml/min; (internal standard: 3,5-dihydroxytoluene $t_R$ 5.60 minutes)

(h) Some of the $^1$H NMR data obtained after $D_2O$ exchange and selective decoupling experiments are as follows (the $^1$H NMR spectrum is registered at 270 MHz in DMSO-$d_6$ at 60° C. and with a sample concentration of 20 mg/ml internal standard, TMS $\delta$=0.00 ppm): ($\delta$ ppm, multiplicity): 1.88, s; 2.85, d; ~3.5, dd; 3–4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d.

(i) a potentiometric titration profile which shows three titration slopes with pH½ values equal to 5.0 (one equivalent), 7.0 (one equivalent), and 11 (five equivalents) in methylcellosolve:water 4:1 upon titration with 0.01N NaOH of the solution of the test compound containing an excess of 0.01N HCl in the same solvent mixture (l) an acidic function capable of forming salts (m) a basic function capable of forming salts (n) two sugar residues which are α-D-mannose and N-acetyl-β-D-glucosamine.

The following examples illustrate the manner in which the invention can be practiced, but, as such, should not be constructed as limiting its overall scope.

EXAMPLE 1

Preparation of antibiotic L 17392 (deglucoteicoplanin) by hydrogenolysis of deglucoteicoplanin benzyl ester, hydrochloride A solution of 4.9 g of essentially pure deglucoteicoplanin benzyl ester hydrochloride, in 500 ml of a $CH_3OH/0.1N$ HCl 7:3 (v/v) solution is hydrogenated at room temperature and pressure in the presence of 3.5 g of 5% Pd/BaSO$_4$. In 30 min about 145 ml of $H_2$ are absorbed. The suspension is filtered and the catalyst is washed thoroughly with 200 ml of a $CH_3OH/H_2O$ 1:1 (v/v) solution, then it is discarded. The filtrates are combined, 600 ml of n-butanol is added and the resulting solution is concentrated to a small volume. By adding acetone a solid separates which is collected, washed with acetone, then with ether, and dried under vacuum at room temperature overnight yielding 4.0 g of essentially pure antibiotic L 17392, hydrochloride.

EXAMPLE 2

Purification of crude antibiotic L 17392

By following the above example but using crude deglucoteicoplanin benzyl ester, crude antibiotic L 17392 is obtained with substantially the same purity as the starting material.

When crude antibiotic L 17392 is obtained, it can be purified according to the following procedure: 5.3 g of crude antibiotic L 17392 (titer 60%) is dissolved in 1 liter of a mixture of 0.2% aqueous ammonium formate/methanol/n-butanol, 1:2:3 (v/v/v) and silanized silica gel (0.06–0.2 mm; Merck 60) (20 g) is added thereto. After appropriate stirring, the solvents are stripped off under vacuum and the residue is applied to the top of a chromatographic column prepared with 750 g of silanized silica gel (0.06–0.2 mm; Merck) in water. The column is developed with 1 l of a mixture of 0.6% aqueous ammonium formate with $CH_3CN$, 9:1 (v/v). The eluate is discarded, then the elution is continued with a linear gradient of acetonitrile in water from 1:9 to 4:6 at a rate of 200 ml/h for about 30 h.

Fractions of 25 ml each are collected and monitored by HPLC. The deglucoteicoplanin containing fractions (200 to 250) are pooled and n-butanol is added. After stirring the mixture is concentrated to a small volume under reduced pressure, ethyl ether is added thereto and the solid which separates is collected by filtration, washed with ethyl ether and dried at 40° C. under vacuum, yielding 0.9 g of essentially pure antibiotic L 17392.

EXAMPLE 3

Preparation of crystalline pure antibiotic L 17392

The pH of a suspension of essentially pure antibiotic L 17392 (0.9 g) in 100 ml of water/acetonitrile, 90:10 (v/v) is brought to 1.7 with 1N hydrochloric acid, at room temperature. The resulting solution is applied to a silanized silica gel column (200 g, 0.06–0.2 mm, Merck 60), equilibrated with 1% aqueous ammonium formate, at a rate of 20 ml/h.

Water (300 ml) is passed through the column and the eluate is discarded. Then the column is developed with a linear gradient of acetonitrile in water from 10% to 40% at a rate of 70 ml/hour for 30 hours. Fraction of 7 ml each are collected and monitored by HPLC.

Antibiotic L 17392 enriched fractions (221–239) are pooled and allowed to stand for 24 hr at room temperature. The solid precipitate is collected by filtration, washed with a small amount (10 ml) of acetonitrile and then with ethyl ether (100 ml) and re-crystallized from a mixture water/acetonitrile 80:20 (v/v). The crystalline solid thus obtained is collected by filtration, washed with ethyl ether and finally dried under vacuum (2 mmHg) for three days yielding 0.55 g of crystalline pure antibiotic L 17392 (colorless needles).

EXAMPLE 4

Preparation of antibiotic L 17392 hydrochloride

Crystalline pure antibiotic L 17392 as obtained in the foregoing example (130 mg) is suspended in a mixture (12 ml) acetonitrile/water), 2:3 (v/v) and 1N hydrochloric acid (0.2 ml) is added thereto. After adding n-butanol (15 ml), the resulting solution is concentrated to a small volume (about 2 ml) under reduced pressure (about 20 mmHg) at 40° C. Ethyl ether (10 ml) is added thereto and the precipitate which forms is collected by filtration, washed with ethyl ether, and dried under reduced pressure at about 50° C., overnight, yielding 107 mg of antibiotic L 17392 hydrochloride.

PREPARATION OF THE STARTING MATERIALS

Preparation of antibiotic deglucoteicoplanin benzyl ester, hydrochloride (a) by treatment of antibiotic L 17046 with benzyl alcohol 1M hydrogen chloride A suspension of 18 g (10 mmol) of essentially pure antibiotic L 17046 in 600 ml of 1M hydrogen chloride in benzyl alcohol is stirred at 60° C. After 15 minutes a clear solution forms which is stirred for additional 3 h at the same temperature, then the solution is cooled to 15° C. and stirring is continued at room temperature for additional 12 h. By adding 4 l of a mixture n-hexane/ether 4:3 (v/v) a solid separates which is collected, washed with 1 l of ether and re-dissolved in 150 ml of methanol. The solution is diluted with 1 l of H₂O and extracted (pH 2.5) twice with 2 l of ethyl acetate. The organic layers are combined and a mixture of 10 ml of 1N HCl in 200 ml of n-butanol is added, then the solution is concentrated in a small volume. By adding 1 l of a mixture n-hexane/ether 3:2 ) (v/v) a solid separates which is collected, washed with ether and dried under vacuum at 40° C. for 8 h yielding 8.5 g of deglucoteicoplanin benzyl ester, hydrochloride (analysis: deglucoteicoplanin benzyl ester, hydrochloride 70%, water and solvents 15%, undefined impurities 15%).

(b) by treatment of the antibiotic L 17054 with 1M hydrogen chloride in 90% aqueous benzyl alcohol To a stirred suspension of 10 g of essentially pure antibiotic L 17054 in 90 ml of benzyl alcohol, 10 ml of 37% hydrochloric acid is added at 40° C. The reaction mixture is heated to 70° C. and stirring is continued for 30 minutes, then water is completely removed under vacuum (about 20 mmHg) at 70° C. (bath temperature). Benzene is added and then the mixture is evaporated under reduced pressure to remove any aqueous residue by means of azeotropic distillation. Then the mixture is diluted with 100 ml of 1M hydrogen chloride in aqueous benzyl alcohol (prepared as above). The clear solution so obtained is stirred at 65° C. for 6 h, then cooled to 15° C. and worked up as described in the foregoing point (a), yielding 4.85 g of deglucoteicoplanin benzyl ester, hydrochloride (analysis: deglucoteicoplanin benzyl ester, hydrochloride 75%, water and solvents 15%, undefined impurities 10%).

(c) by treatment of teicoplanin with 2M hydrochloric acid in 80% aqueous benzyl alcohol, under vacuum and with repeated additions of benzene and 37% hydrochloric acid.

To a stirred suspension of 10 g of teicoplanin (content in teicoplanin components: 85%) in 80 ml of benzyl alcohol, 20 ml of 37% hydrochloric acid is added at 40° C. The mixture is kept under vacuum (about 20 mmHg) for about 60 minutes while heating to about 65° C. (bath temperature), then 50 ml of benzene is added and the mixture is evaporated under vacuum at about 65° C. After 30 minutes, a mixture of 5 ml of 37% hydrochloric acid in 25 ml of benzyl alcohol is added to the reaction mixture which is then re-submitted to the "under vacuum" procedure (about 20 mmHg; about 65° C.) for 30 minutes. Then 50 ml of benzene is added and evaporated as previously described. Alternate additions of mixtures of 5 ml of 37% hydrochloric acid in 15 ml of benzyl alcohol and of 50 ml of benzene separated by the "under vacuum" procedure are repeated every 30 minutes for 8 hours. Then 20 ml of 37% hydrochloric acid and 100 ml of benzene are added, while water and benzene are evaporated under vacuum and the resulting clear solution is stirred at room temperature and pressure under argon atmosphere for 12 h, then the reaction mixture is poured into 1.5 l of ether. A solid separates which is collected, washed with ether and dried under vacuum at room temperature overnight, yielding 10 g of the crude ester of the title. This product is dissolved in 150 ml of methanol and 300 ml of water and 300 ml of ethyl acetate are added thereto with vigorous stirring. After few minutes additional 300 ml of water, 300 ml of ethyl acetate and a mixture of 300 ml of n-butanol/water 1:2 (v/v) were added. The pH of the aqueous layer is adjusted to 3.5 and the organic phase is separated. The aqueous phase is extracted twice with ethyl acetate (600 ml each time). The organic layers are combined, washed with 400 ml of water and concentrated to a small volume under vacuum. By adding ether a solid separates which is collected, washed with ether and dried under vacuum at room temperature overnight, yielding 6.1 g of crude deglucoteicoplanin benzyl ester, hydrochloride (analysis: deglucoteicoplanin benzyl ester, hydrochloride 65%; water and solvents 15%, undefined impurities 20%).

PURIFICATION OF DEGLUCOTEICOPLANIN BENZYL ESTER BY SILICA-GEL COLUMN CHROMATOGRAPHY

Silica-gel (0.06–0.2 mm, Merck 60) (10 g) is added to a solution of 2.5 g of crude deglucoteicoplanin benzyl ester (titer 65%) in 100 ml of 90% aqueous methanol. The solvent is completely evaporated under vacuum and the residue is applied to a chromatographic column containing 250 g of silica-gel slurried in acetonitrile. The column is developed by sequentially using the following solvent mixtures:

| | |
|---|---|
| CH₃CN | 250 ml |
| CH₃CN/H₂O 97:3 (v/v) | 500 ml |
| CH₃CN/H₂O 94:6 (v/v) | 500 ml |

The eluates are discarded, then the column is eluted with a linear gradient of acetonitrile in water obtained by mixing 1.5 l each of the solvent mixtures CH₃CN/H₂O 94:6 (v/v) and CH₃CN/H₂O 70:30 (v/v) at a rate of 200 ml/h. Fractions of 25 ml are collected and assayed by HPLC. Deglucoteicoplanin benzyl ester containing fractions are combined (700 ml), n-butanolic 0.05M hydrogen chloride (250 ml) is added thereto, and the solvents are evaporated up to a final volume of about 30 ml. By adding either (300 ml) a solid separates which is collected, washed with ether and dried under vacuum at 40° C. for 48 h, yielding 1.6 g of essentially pure deglocoteicoplanin benzyl ester, hydrochloride.

By operating essentially following the procedures of the above examples and employing the suitable reagents the following starting materials can be obtained:
deglucoteicoplanin 4-chlorobenzyl ester
deglucoteicoplanin 2,4-chlorobenzyl ester
deglucoteicoplanin 4-nitrobenzyl ester
deglucoteicoplanin 3,4-nitrobenzyl ester
and the acid addition salts thereof.

We claim:

1. A process for preparing antibiotic L 17392 which has the following characteristics
   (a) it is soluble in water at a pH higher than 9 and aqueous methanol, ethanol and acetone; slightly soluble in ethyl alcohol and dimethylformamide
   (b) an ultraviolet absorption maxima which shows the following absorption maxima:
      in 0.1N hydrochloric acid: $\lambda_{max}$ 279 nm ($E_1\ cm^1\% = 87.1$)
      in 0.1N sodium hydroxide: $\lambda_{max}$ 297 nm ($E_1\ cm^1\% = 165.3$)
   (c) an infrared absorption spectrum in nujol with the following mainly significant absorption maxima (cm$^{-1}$):
      3250 ($\nu$ NH; and phenolic $\nu$ OH)
      1645 (Amide I)
      1610 ($\nu$ COO$^-$)
      1595 ($\delta$ NH$_3^+$)
      1520 (Amide II)
   (d) Some of the ¹H NMR data obtained after D₂O exchange and selective decoupling experiments of the $^1$H NMR spectrum registered at 270 MHz with a Bruker WH-270 Spectrometer, in DMSO-$d_6$ at 50° C. (internal standard TMS, δ=0.00 ppm) are as follows (δ, multiplicity): 2.85–3.30, 2dd; 4.12, dd; 4.37, d; 4.45, d; 4.50, s; 5.00, ddd; 5.11, d; 5.14, d; 5.35, d; 5.56, d; 5.60, d; 6.3–7.9, m; 6.55, d; 7.37, d; 7.50, d; 7.61, d; 8.26; d; 8.28, d; 8.5–10.2, br;

d=doublet
dd=doublets of doublets
ddd=doublet of doublets of doublets
s=singlet
m=multiplet
br=broad (e) an elemental analysis which indicates the following approximate percentage composition (average): carbon 58.05%; hydrogen 3.58%; nitrogen 8.23%; chlorine 5.85%; (after correction for a weight loss of 11%, measured by thermal gravimetric analysis)

(f) a molecular weight of 1199 confirmed also by FAB-MS analysis (g) the following formula [calculated on the basis of the available data]:

$C_{58}H_{45}Cl_2N_7O_{18}$ (h) a retention time ($t_R$) of 12.2 min when analyzed by HPLC using a pre-column (5 cm) packed with Perisorb RP-8 (30 μm; Merck) followed by a column Hibar RT 250-4 (Merck) prepacked with Li-Chrosorb RP-8 (10 μm) and eluting with a liner step-gradient ranging from 10% to 30% acetonitrile in 0.2% aqueous ammonium formate; flow rate: 2 ml/min. (internal standard: Teicoplanin $A_2$ component 2, $t_R$=22.4 min)

(i) an acidic function capable of forming salts
(l) a basic function capable of forming salts
(m) no sugar residue
(n) the following putative chemical formula:

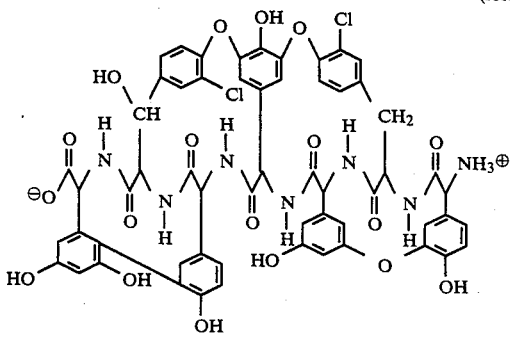

(formula I)

which comprises submitting a deglucoteicoplanin ester of formula II

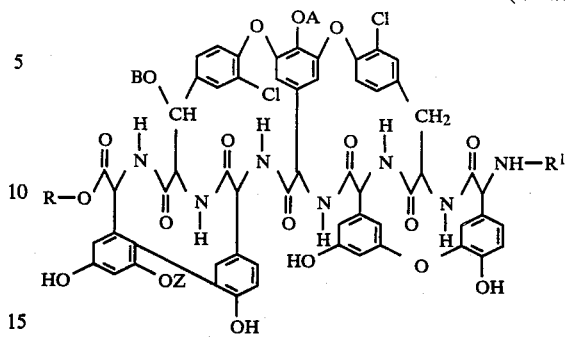

(formula II)

wherein A, B and Z represent hydrogen atoms, R represents benzyl or substituted benzyl, wherein the phenyl group is substituted with at least a substituent selected from chloro, bromo, fluoro, nitro, ($C_1$-$C_3$)alkyl and ($C_1$-$C_3$)alkoxy, with the exclusion of the tri-nitro phenyl group, R' is H, or acid addition salts thereof, to catalytic hydrogenolysis in the presence of a poisoned hydrogenation catalyst at a temperature from 10° C. to 40° C. and a pressure between ambient pressure and 5 atm, in an inert organic solvent in the presence of a mineral acid.

2. A process according to claim 1 wherein the catalyst is a poisoned catalyst selected from Palladium, nickel, Copper, and Cobalt either at the zero-valent status or with a positive oxidation number on a suitable support.

3. A process according to claim 1 wherein the poisoned catalyst is Palladium on carbon, barium carbonate or calcium sulfate.

4. A process according to claim 1 wherein the poisoned catalyst is 5–10% Palladium on Barium sulfate.

5. A process according to claim 1 wherein the poisoned catalyst is 5% Palladium on Barium sulfate.

6. A process according to claim 1 wherein the inert organic solvent is selected from methanol, ethanol, dioxane, ethylene glycol and ethylene glycol monomethylether.

7. A process according to claim 1 wherein the mineral acid is hydrochloric acid.

8. A process according to claim 1 wherein the temperature is room temperature.

9. A process according to claim 1 wherein the pressure is the ambient pressure.

10. A process according to claim 1 wherein the starting material of formula II is deglucoteicoplanin benzyl ester or an acid addition salt thereof.

11. A process according to claim 1 which further comprises suspending the substantially pure amorphous antibiotic L 17392 product in a mixture of water and acetonitrile, 9:1 at a pH of about 1.7, the pH being adjusted by adding 1N hydrochloric acid, purifying the resulting solution by column chromatography, and leaving set aside for about 24 hours the pooled antibiotic L 17392 containing fractions to permit the precipitation of crystalline antibiotic L 17392.

* * * * *

UNITED STATES PATENT AND TRADEMARK OFFICE
CERTIFICATE OF CORRECTION

PATENT NO.: 4,882,419

DATED: 11/21/89

INVENTOR(S) : Malabarba et al.

It is certified that error appears in the above-identified patent and that said Letters Patent is hereby corrected as shown below:

The patent reads "glycosamine" at Column 7, line 63, and should read "glucosamine".

The patent reads "7.90" at Column 10, line 8, and should read "7.09".

The patent reads "1995" at Column 10, line 39, and should read "1595".

The patent reads "either" at Column 14, line 35, and should read "ether".

The patent reads "deglocoteicoplanin" at Column 14, line 38, and should read "deglucoteicoplanin".

Signed and Sealed this

Twenty-ninth Day of October, 1991

Attest:

HARRY F. MANBECK, JR.

*Attesting Officer*  *Commissioner of Patents and Trademarks*